United States Patent [19]
Winkler

[11] Patent Number: 5,544,127
[45] Date of Patent: *Aug. 6, 1996

[54] BOREHOLE APPARATUS AND METHODS FOR MEASURING FORMATION VELOCITIES AS A FUNCTION OF AZIMUTH, AND INTERPRETATION THEREOF

[75] Inventor: Kenneth W. Winkler, Ridgefield, Conn.

[73] Assignee: Schlumberger Technology Corporation, Ridgefield, Conn.

[*] Notice: The term of this patent shall not extend beyond the expiration date of Pat. No. 5,398,215.

[21] Appl. No.: 220,717

[22] Filed: Mar. 30, 1994

[51] Int. Cl.$^6$ .................................................. G01V 1/00
[52] U.S. Cl. ............................. 367/27; 367/86; 181/104
[58] Field of Search ................................. 367/25, 27, 86; 181/104

[56] References Cited

U.S. PATENT DOCUMENTS

| | | | |
|---|---|---|---|
| 3,611,278 | 10/1971 | Guinzy | 367/25 |
| 3,697,937 | 10/1972 | Ingram | 367/25 |
| 4,415,998 | 11/1983 | Blizard | 367/25 |
| 4,641,520 | 2/1987 | Mao | 367/25 |
| 4,740,928 | 4/1988 | Gutowski et al. | 367/27 |
| 4,774,693 | 9/1988 | Winbow et al. | 367/27 |
| 4,775,960 | 10/1988 | Staron et al. | 367/27 |
| 4,791,618 | 12/1988 | Pruchnik | 367/25 |
| 4,791,619 | 12/1988 | Liu | 367/27 |
| 4,819,214 | 4/1989 | Gutowski et al. | 367/27 |
| 4,832,148 | 5/1989 | Becker et al. | 181/104 |
| 4,845,616 | 7/1989 | Phillips | 367/27 |
| 4,870,627 | 9/1989 | Hsu et al. | 367/25 |
| 5,081,611 | 1/1992 | Hornby | 367/25 |
| 5,168,470 | 12/1992 | Dennis et al. | 367/25 |
| 5,198,770 | 3/1993 | Decorps et al. | 367/25 |
| 5,208,785 | 5/1993 | Brumley et al. | 367/90 |
| 5,398,215 | 3/1995 | Sinha et al. | 367/27 |
| 5,450,371 | 9/1995 | MacKay | 367/27 |

OTHER PUBLICATIONS

"Numerical Evaluation of the Transient Acoustic Wave Form Due to a Point Source in a Fluid–Filled Borehole", Tsang and Rader, Geophysics 44, No. 10 pp. 1706–1720 (1979).
"Acoustic Multipole Sources in Fluid–Filled Boreholes", Kurkjian Chan Geophysics 51, No. 1, pp. 148–163 (1986).
"Interaction of Elastic Waves in a Isotropic Solid", Jones & Kobbet, Jour. Acoustic Soc. Am. 35, No. 1, pp. 5–10 (1963).
"Ultrasonic Study of Three–Phonon Interactions. I. Theory", Taylor & Rollins, Phys. Rev. 136, No. 3A, pp. 591–596 (1964).

(List continued on next page.)

Primary Examiner—Charles T. Jordan
Assistant Examiner—Theresa M. Wesson
Attorney, Agent, or Firm—David P. Gordon; Martin D. Hyden; Leonard W. Pojunas

[57] ABSTRACT

Borehole tools are provided with at least one transmitter which generates acoustic waves at a plurality of azimuthal locations about the borehole, and at least one receiver which receives and measures a characteristic (e.g., velocity) of the acoustic waves at related azimuthal locations. The direction of minimum velocity around the borehole is considered the direction of maximum uniaxial stress in the formation. From the velocity as a function of azimuth information, determinations of formation properties, and logs of the same can be made. The azimuthal direction of minimum velocity around the borehole predicts the propagation direction of artifically induced hydrofractures. The velocity variation around the borehole at a particular depth of the borehole is taken as an indication of susceptibility to failure, with higher velocity variations indicative of a more poorly consolidated formation or a formation with a large uniaxial stress. The curvature of the velocity versus stress curve in the formation is also indicated by how poorly a sine wave fits to the velocity data. Other parameters of the formation are obtained by fitting a best fit curve to the azimuth versus velocity data, where adjustable parameters of the best fit curve constitute the formation parameters.

28 Claims, 7 Drawing Sheets

OTHER PUBLICATIONS

Non-linear Phenomena in the Propagation of Elastic Waves in so Zarembo & Krasilnikon, Sev. Phys. Usp. 13, No. 6, pp. 778–797 (1971).

"Harmonic Generation of Longitudinal Elastic Waves", Thompson Tiersten, J. Acoust. Soc. Am 62, No. 1, pp. 33–37 (1977).

"Non–Linear Rayleigh Waves: Harmonic Generation, Parametric Amplification and Thermoniscous Damping", Lardner, J. Appl. Phys. 55 No. 9, pp. 3251–3260 (1984).

"Nonlinear Properties of Rayleigh and Staneley Waves in Solids", Shui & Solodov, J. Appl. Phys. 64 No. 11, pp. 6155–6165 (1988).

"Second–Order Elastic Deformation of Solids", Hughes & Keys Phys. Rev. 92, No. 5 pp. 1145–1149 (1953).

"Third Order Elastic Constants and the Velocity of Small Ampliture Elastic Waves in Homogemeously Stressed Mcdia", Thurston & Brugger, Phys. Rev. 133, No. 6A, pp. 1604–1610 (1964).

"Sound Waves in Deformed Perfectly Elastic Matericts Acoustoela Effect", Toupin & Bernstein, J. Acoust. Soc. Am. 33, No. 2, pp. 210–225.

"Parameter of Nonlinearity in Fluids. II", Coppens et al, J. Acoust. Soc. Am. 38, pp. 797–804 (1965).

"Pressure & Temperature Dependence of the Acoustic Velocities of Polymethylmethacrylate", Asay et al, J. Appl. Phys. No. 4, pp. 1768–1783 (1969).

"Third Order Elastic Constants of Ge, MgO and Fused $SiO_2$", Bogardus, J. Appl. Phys. 38, No. 8, pp. 2504–2513 (1965).

"Third–Order Elastic Moduli of Polycrystalline Metals From Ultrasonic Velocity Measurements", Smith et al, J. Acoust. Soc. Am. 40, No. 5, pp. 1002–1008 (1966).

"Ultrasonic Wave Velocities in Stressed Nickel Steel", Crecroft, Nature 195, pp. 1193–1194 (1962).

"Third Order Elastic Constants of Single–Crystal and Polycrystalline Columbium", Graham et al. J. Appl. Phys. 39, No. 7, pp. 3025–3033 (1968).

"Sound Velocity Measurements at High Pressures", Mongomery et al, Rev. Sci. Instr. 38, No. 8, pp. 1073–1076 (1967).

"Velocity of Seismic Waves in Porous Rocks", Toksöz et al, Geophysics 41, No. 4, pp. 621–645 (1976).

Linear & Nonlinear Waves, Whitham, John Wiley & Sons New York 1974.

"Parameter of Nonliearity in Fluids", Beyer, J. Acoust. Soc. Am. 32, No. pp. 719–721 (1960).

Thermodynamic Definition of Higher Order Elastic Constants", Brugger, Phys. Rev. 133, No. 6A, pp. 1611–1612 (1964).

"Finite Deformations of an Elastic Solid", Murnaghan, Chapman & Hall, NY 1951 pp. 89–95.

Ultrasonic Investigation of Mechanical Properties, Green, Academic Press, Ny 1973 pp. 73–145.

"Wave Velocities in Rocks as a Function of Changes in Overbearing Pressure and Pore Fluid Saturants", King, Geophysics 31 No. 1, pp. 50–73 (1966).

"Interaction of Plane Longitudinal & Transverse Elastic Waves", Sov. Phys. Acoust. 6, pp. 306–310 (1961).

Nonlinear Generation of Elastic Waves in Franite & Sandstone: Continuous Wave and Travel Time Observations, Johnson et al. J. Geophysics Res. B. 94, pp. 17729–17733 (1989).

Continuous Wave Phase Detection for Probing Nonlinear Elastic Wave Interactions in Rocks, Johnson et al. J. Acoust. Soc. Am 89, No. 2, pp. 598–603 (1991).

Nonlinear Generation of ELastic Waves in Chrystalline Rock", Johnson et al, J. Geophysics Res.B.92, pp. 3597–3602 (1987).

Physical Ultrasonics, Beyer et al, Academic Press, NY (1969) vol. 32 of Pure & Applied Physics.

Theory of Elasticity, Landau et al, Pegamon Press, Oxford 1986 3rd edition pp. 106–107.

Pressure Derivatives of the Sound Velocities of Polycrystalline Alumina, Schreiber et al, Jour. Amer. Ceram. Soc. 49 pp. 184–190 (1966).

"Effects of Stress on Velocity Anistrophy in Rocks with Cracks", by Nur, Jour. of Geophysical Research, vol.76, No. 8, pp. 2022–2034.

"The Effect of Oriented Cracks on Seismic Velocities", by Anderson, Jour. of Geophysical Research, vol. 79, No. 26 pp. 4011–4015.

"Changers in Seismic Velicity & Attenuation During Deformation of Granite", Lockner et al. Jour. of Geophysical Research, vol. 82, No. 33, Nov. 10, 1977 pp. 5374–5378.

∂Stresses Around a Deep Well" by Miles et al., Trans. AIME, 179, (1948) pp. 186–191.

"Corre lation of Longitudinal Velocity Variation with Rock Fabric", Thill et al. J. of Geophysical Research, vol. 74, No. 20, (1969) pp. 4897–4909.

"Stress–Induced Velocity Anisotropy in Rock: An Experimental Study" by Nur et al. J. of Geophysical Research, vol. 74, Dec. 1969, pp. 6667–6674.

*Fundamentals of Rock Mechanics,* by Jaeger & Cook, c:1969, Chapman and Hall, Ltd, Chapter 15, pp. 363–383.

BOREHOLE APPARATUS AND METHODS FOR MEASURING FORMATION VELOCITIES AS A FUNCTION OF AZIMUTH, AND INTERPRETATION THEREOF

BACKGROUND OF THE INVENTION

This application relates to co-owned U.S. Ser. No. 8/154,645, filed on Nov. 19, 1993, which is hereby incorporated by reference herein in its entirety.

BACKGROUND OF THE INVENTION

1. Field of the Invention

This invention relates broadly to methods and apparatus for investigating subsurface earth formations. More particularly, this invention relates to sonic borehole tools and methods for measuring formation velocities and hence stresses around a borehole as a function of azimuth, wherein properties of the formation are determined from the velocity or stress distribution.

2. State of the Art

The art of sonic well logging for use in determining formation parameters is a well established art. Sonic well logs are typically derived from sonic tools suspended in a mud-filled borehole by a cable. The tools typically include a sonic source (transmitter) and a plurality of receivers which are spaced apart by several inches or feet. Typically, a sonic signal is transmitted from the transmitter at one longitudinal end of the tool and received by the receivers at the other, and measurements are made every few inches as the tool is drawn up the borehole. The sonic signal from the transmitter or source enters the formation adjacent the borehole, and the arrival times of the compressional (P-wave), shear (S-wave) and Stoneley (tube) waves are detected by the receivers. The receiver responses are typically processed in order to provide a time to depth conversion capability for seismic studies as well as for providing the determinations of formations parameters such as porosity.

It has long been known that the drilling of a borehole into a formation disturbs the stress field that was present in the formation prior to the existence of the borehole. The drilling of the borehole results in circumferential and radial stress concentrations around the borehole, where the resulting stress field is strongly anisotropic at the borehole wall, but the effects of the borehole decrease rapidly with distance into the formation. It has also been established that acoustic velocities in rock are sensitive to applied stress, with both compressional and shear velocities increasing with hydrostatic stress. Uniaxial stress produces compressional and shear wave anisotropy and shear wave birefringence (velocity dependent on polarization). These results have been related by A. Nur, "Effects of Stress on Velocity Anisotropy in Rocks with Cracks", *Journal Geophysics. Res.;* Vol. 76, 8, p. 2022 (1971), and by D. L. Anderson et al., "The Effect of Oriented Cracks on Seismic Velocities", *Journal Geophysics Res.;* Vol. 82 p.5374 (1974), to stress-induced anisotropy of microcrack orientations.

Despite the knowledge which has been accumulated over the years regarding stress fields in formations, sonic borehole tools having never been used to measure the stress fields around the borehole as a function of azimuth, and stress field distribution information has never been used in order to determine directions of maximum tectonic stress in the formation.

SUMMARY OF THE INVENTION

It is therefore an object of the invention to provide sonic borehole tools and methods for measuring formation velocity as a function of azimuth about a borehole.

It is a further object of the invention to provide a log of the velocities and stress fields about a borehole as a function of azimuth by measuring the sonic compressional wave velocities about the borehole.

It is another object of the invention to relate observed azimuthal velocity variations to the direction of maximum compressive stress perpendicular to the borehole, and thereby to predict the direction of hydrofracture propagation.

It is an additional object of the invention to derive an indication of the degree of consolidation of the formation from a percent velocity variation measured about the borehole.

Another object of the invention is to obtain indications of a formation parameter by measuring velocity information of the formation as a function of azimuth and comparing that information to a sine wave or a model fit fitted to the obtained data.

In accord with the objects of the invention, the borehole tool of the invention comprises a transmitter means for generating acoustic waves at a plurality of azimuthal locations about the borehole, a receiver means for receiving the acoustic waves at related azimuthal locations, and a processor means coupled to the receiver means for determining the acoustic velocities of the formation around the borehole as a function of azimuth and for generating at least one stress field indication as a result thereof. The stress field indications are preferably used to provide the likely direction of hydrofracture propagation, as well as other parameters of the formation such as the susceptibility of the borehole to collapse.

According to the invention, various embodiments of the borehole tool are possible. A first embodiment includes a segmented cylindrical transmitter and either at least two spaced simple ring transducer receivers or at least to axially spaced segmented cylindrical receivers. Via electronic control, the segments of the cylindrical transmitter are fired sequentially, and velocity measurements for each transmitted signal are made at at least the corresponding azimuths of the axially spaced receivers, and possibly at all azimuths. A second embodiment of the invention comprises a pad tool having transmitters and receivers which are mounted on a plurality of pads that are pressed against the borehole wall. Two axially spaced receivers are preferably provided for each transmitter. Since the receivers on each pad correspond to transmitters located at the same azimuth, it is possible to fire a plurality of the transmitters at the same time and make simultaneous velocity measurements at the receivers. A third embodiment of the invention utilizes a tool having a transmitter and two receivers which are mounted on the side of the tool and aimed at the borehole wall. The tool, or at least a portion thereof containing the transmitter and receivers is rotatable in the borehole so that acoustic velocity measurements may be made at a plurality of azimuths around the borehole.

Once measurements have been made with the borehole tool, the direction of minimum stress around the borehole may be obtained from the azimuth of minimum velocity;

with the azimuth of minimum velocity around the borehole corresponding to the direction of maximum uniaxial stress in the formation perpendicular to the borehole. While visual inspection of the velocity data versus azimuth is generally sufficient, a sine wave (sin2Θ) may be fit to the curve relating azimuth to formation velocity to find minima. These minima will predict the propagation direction of artificially induced hydrofractures, which will aid in the development of low permeability hydrocarbon reservoirs. Additional information besides azimuth of minimum velocity about the borehole is also obtained from the data. For example, velocity variation around the borehole can be taken as an indication of the susceptibility of the borehole to failure. Higher variations in velocity are indicative of a more poorly consolidated or a formation with a large uniaxial stress; either of which may be used to warn of a potential borehole collapse. Additional information is obtained by comparing the formation velocity data as a function of azimuth to a sine wave fitted to the data. If the sine wave fits closely to the data, then the velocity is linearly proportional to the stress. However, larger deviations are indicative of a nonlinear velocity versus stress relationship in the formation. Other parameter of the formation may be obtained by fitting a best fit curve to the azimuth versus velocity data, where adjustable parameters of the curve constitute the formation parameters.

According to a preferred aspect of the invention, compressional waves are used to measure the acoustic velocity of the formation. It should be appreciated, however, that shear waves and high-frequency flexural waves may also be utilized.

Additional objects and advantages of the invention will become apparent to those skilled in the art upon reference to the detailed description taken in conjunction with the provided figures.

BRIEF DESCRIPTION OF THE DRAWINGS

FIG. 2b is the plot of FIG. 2a after normalization to the zero stress data in FIG. 2a.

DETAILED DESCRIPTION OF THE PREFERRED EMBODIMENTS

Figure 1A:
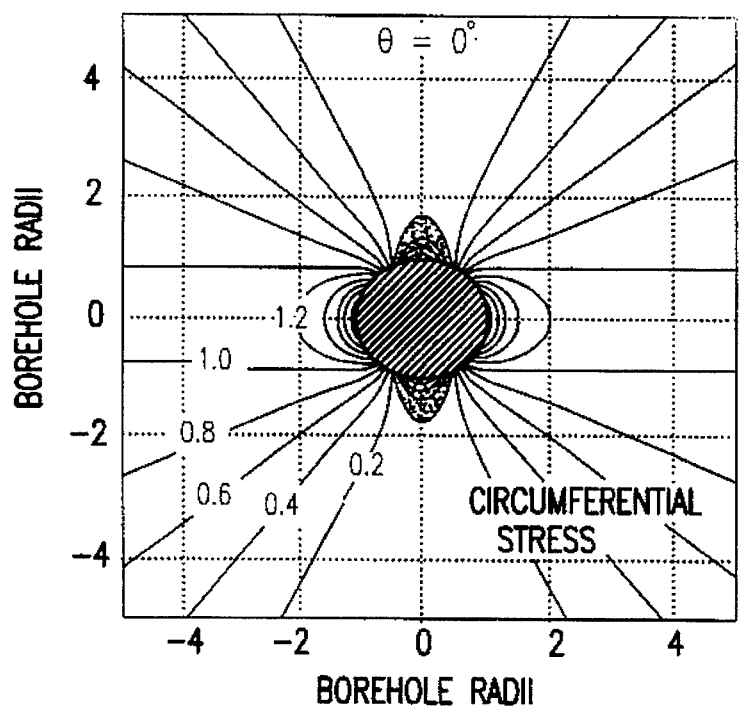
FIG. 1a is a plot of circumferential stress as a function of borehole azimuth, where the circumferential stress is due to a unit uniaxial stress applied perpendicular to the borehole.
Figure 1B:
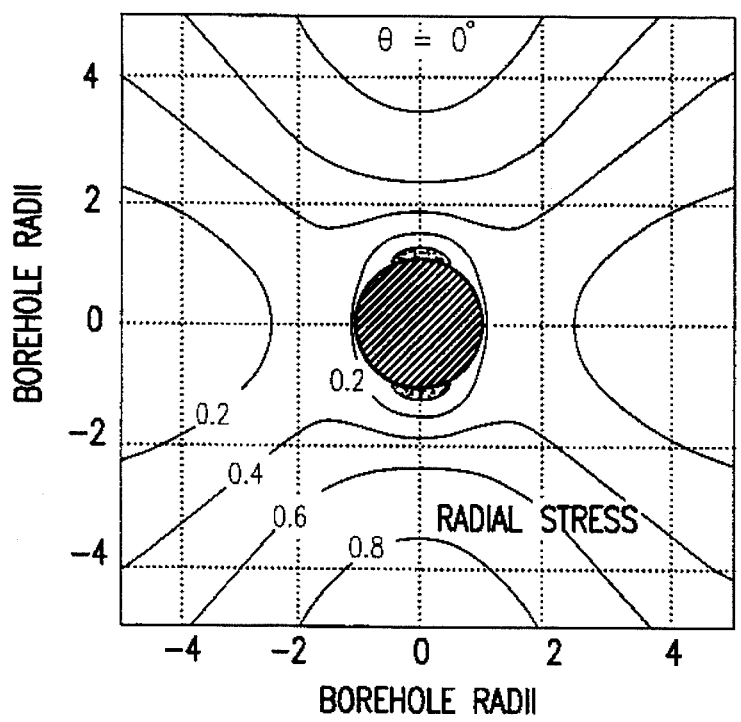
FIG. 1b is a plot of radial stress as a function of borehole azimuth, where the radial stress is due to a unit uniaxial stress applied perpendicular to the borehole.

It has been well known for some time that earth formations are subject to stresses which can take a preferred direction. Because these stresses take a preferred direction, the formation may be viewed as having a uniaxial stress in that preferred direction superimposed on an isotropic stress that does not vary with direction. If it assumed that the formation under a uniaxial stress behaves elastically, then existing equations can be used to describe the stresses which occur around a circular borehole. In particular, the circumferential stress $\sigma_{\sigma+}$ and the radial stress $\sigma_r$ which result from the drilling of a borehole in a formation are defined according to:

$$\sigma_\sigma = S/2\{[1+(b^2/r^2)]-[1+(3b^4/r^4)]\cos 2\Theta\}$$

$$\sigma_r = S/2\{[1-(b^2/r^2)]+[1-(4b^2/r^2)+(3b^4/r^4)]\cos 2\Theta\}$$

where S is the magnitude of the applied stress, b is the borehole radius, r is the radial distance into the formation from the center of the borehole, and Θ=0 is the direction of the applied stress. Using equations (1) and (2) above, the circumstantial and radial stresses are plotted as a function of borehole azimuth in FIGS. 1a and 1b, where the circumstantial stress is due to a unit uniaxial stress applied perpendicular to the borehole. As is seen in FIG. 1a, the circumstantial stress is highly compressive along Θ=90° and 270°, and tensile (being shown by shading) near the borehole along Θ=0°. As seen in FIG. 1b, radial stress is also tensile (again shown by shading) near the borehole along Θ=0°.

Based on FIGS. 1a and 1b, it would appear that a relative uniaxial stress (superimposed on any isotropic stress) might produce measurable changes in velocity with azimuth in earth (rock) formations. To test this thesis, a Berea sandstone sample and a Hanson sandstone sample were obtained and borehole type holes were cut through the samples. The samples were then subjected to known amounts of uniaxial stress, with sample velocity measurements being obtained via use of a borehole type sonic tool. The borehole type sonic included a transmitter and two axially spaced receivers, and the borehole type sonic tool was rotated about its own axis in small increments so that velocity measurements could be obtained as a function of azimuth.

Figure 2A:
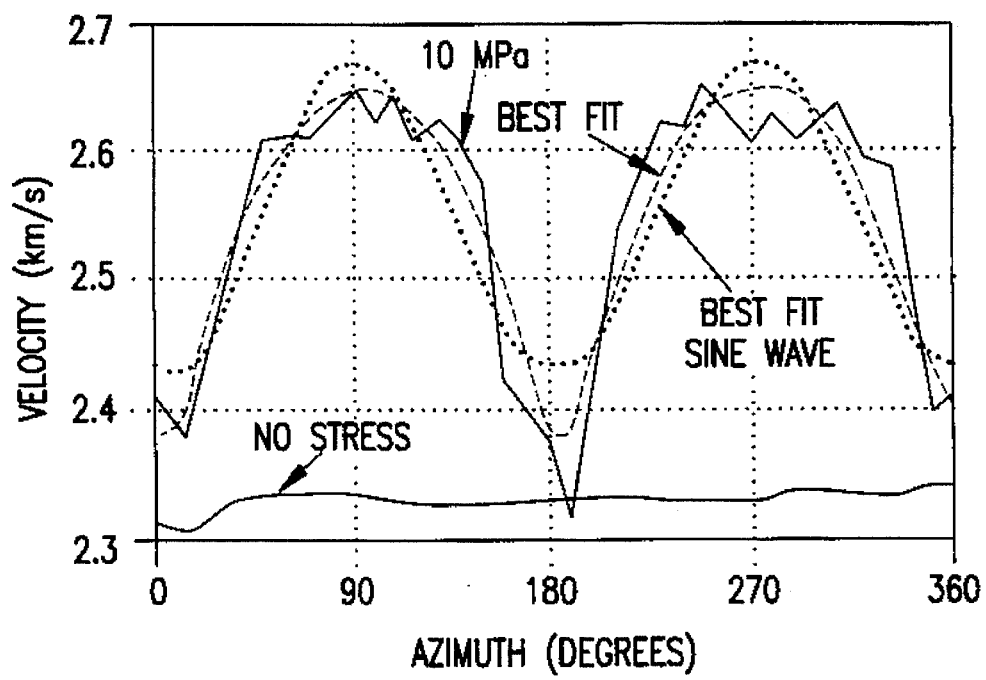
FIG. 2a is a plot of velocity versus azimuth for a Berea sandstone sample which was placed under uniaxial stress in a test procedure.

The results of the tests conducted are seen in FIGS. 2a, 2b, 3a, and 3b. As seen in FIG. 2a, plots of compressional wave velocity in km/s as a function of azimuth were obtained for a Berea sandstone as a baseline where no uniaxial stress was applied, and where a 10 MPa (megapascal) uniaxial stress was applied. The baseline readings for the non-application of stress were taken for normalization purposes. With this information, the 10 MPa data which are plotted in FIG. 2a are shown in a normalized format in FIG. 2b. It should be appreciated that in the normalized plot of FIG. 2b, the compressional wave velocity is seen to vary in a range of up to between ten and fifteen percent; an amount which should be readily detectable by a sonic borehole tool.

Figure 2B:
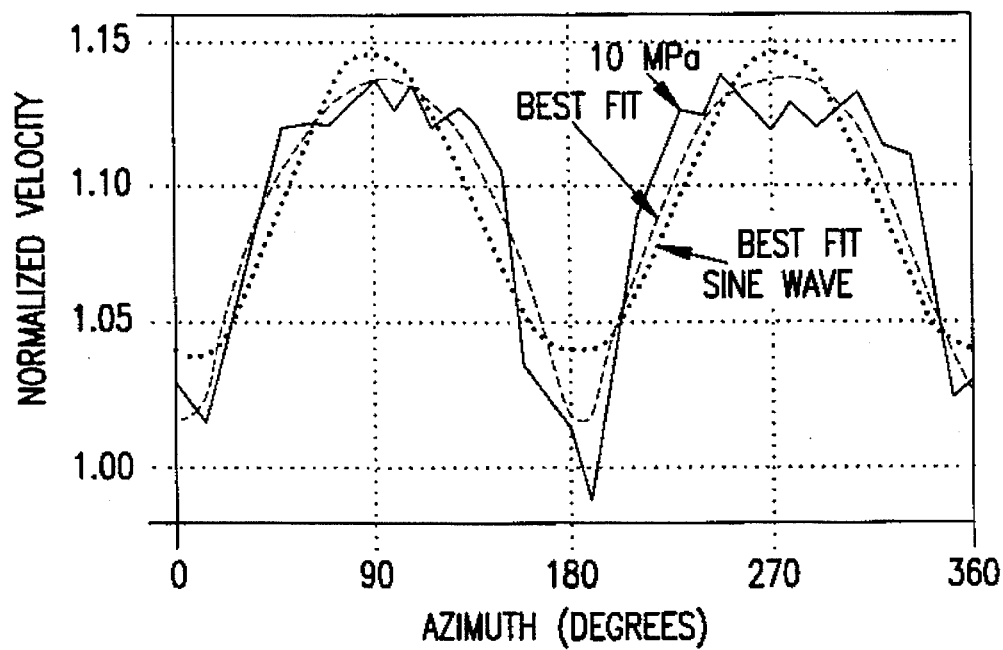

In addition to the actual data, and as will be discussed in more detail below, a best fit sine wave and a best fit curve for the data (both pre-normalized and normalized) are seen in FIGS. 2a and 2b. As will be appreciated by a cursory review of the pre-normalized and normalized data, as well as by viewing the fitted sine wave and best fit curve, the azimuthal locations of lowest velocity were at zero and one hundred eighty degrees about the "borehole", while the azimuthal locations of highest velocity were at ninety and two hundred and seventy degrees about the "borehole". Provided that the velocity increases as stress increases (which is discussed below with reference to FIG. 4), these results meet the expectations which result from FIGS. 1a and 1b where circumferential and radial stress are lowest at zero and one hundred and eighty degrees, and highest at ninety and two hundred and seventy degrees.

Figure 3A:
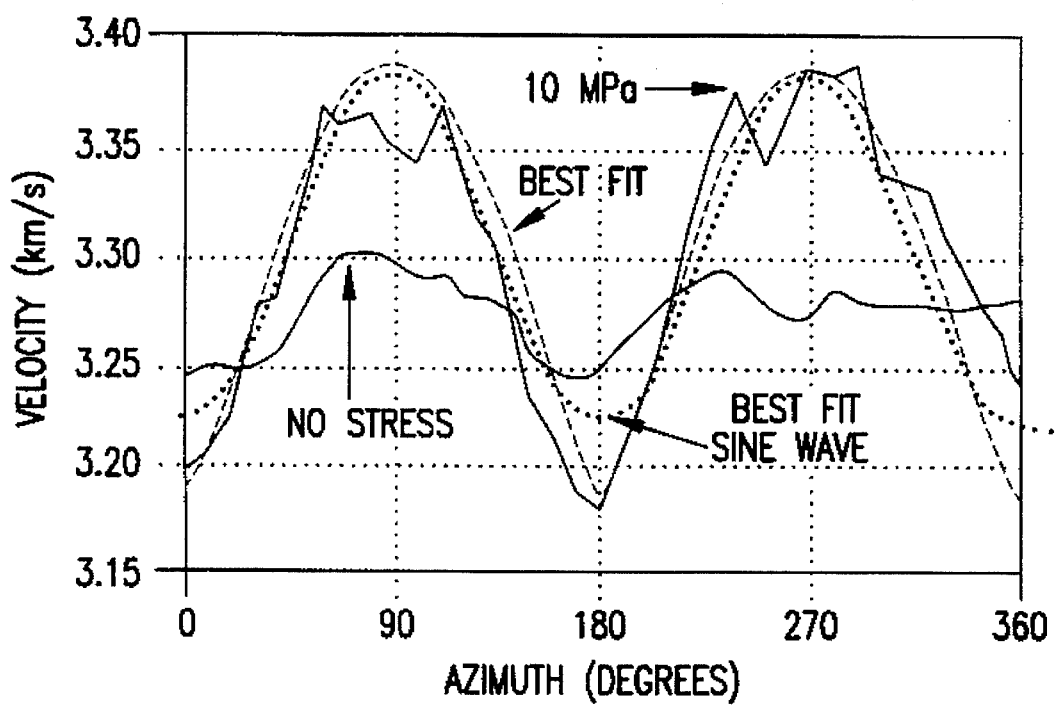
FIG. 3a is a plot of velocity versus azimuth for a Hanson sandstone sample which was placed under uniaxial stress in a test procedure.
Figure 3B:
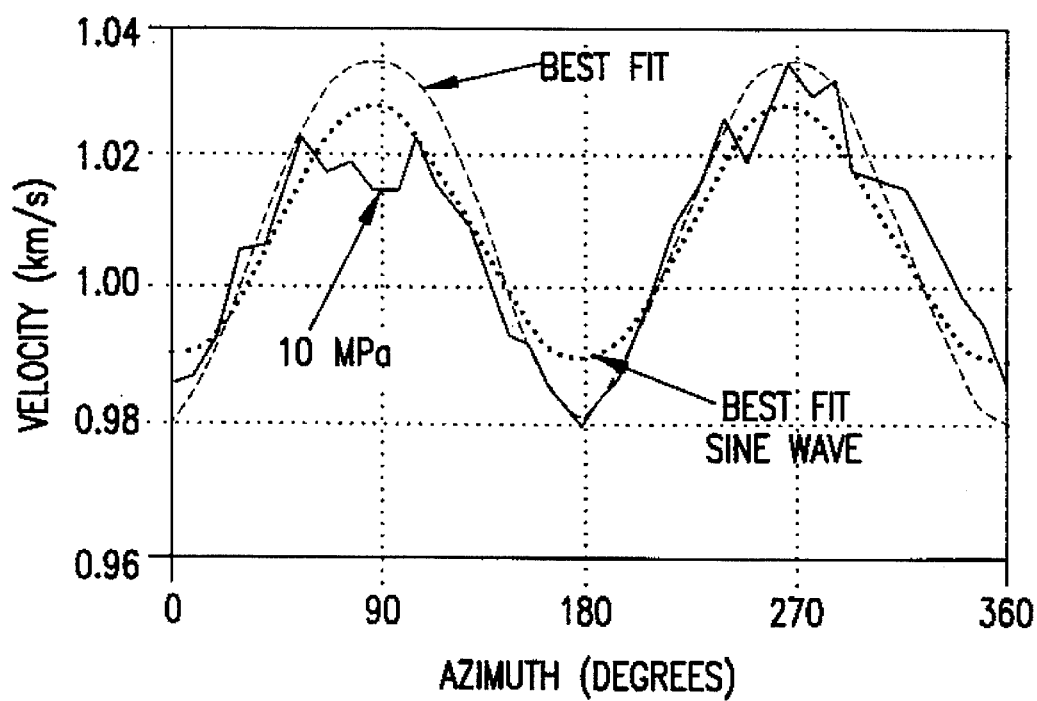
FIG. 3b is the plot of FIG. 3a after normalization.

The results obtained in the Hanson sandstone sample as seen in FIGS. 3a and 3b are similar to the results obtained in the Berea sandstone sample. The primary differences in results relate to the actual velocities detected, the range (in percentage) in which the velocities vary, and the fact that the normalized velocity shows a below one reading in velocity at and around the zero and on hundred eighty degree azimuthal locations. However, the faster velocities detected in the Hanson sandstone are expected in that Hanson sandstones are typically more consolidated than Berea sandstones. Also, while the range in velocities around the borehole in the Hanson sandstone sample are smaller than the velocity range in the Berea sandstone, the range is still up to five percent, and should be detectable by a sonic borehole tool.

Figure 4:
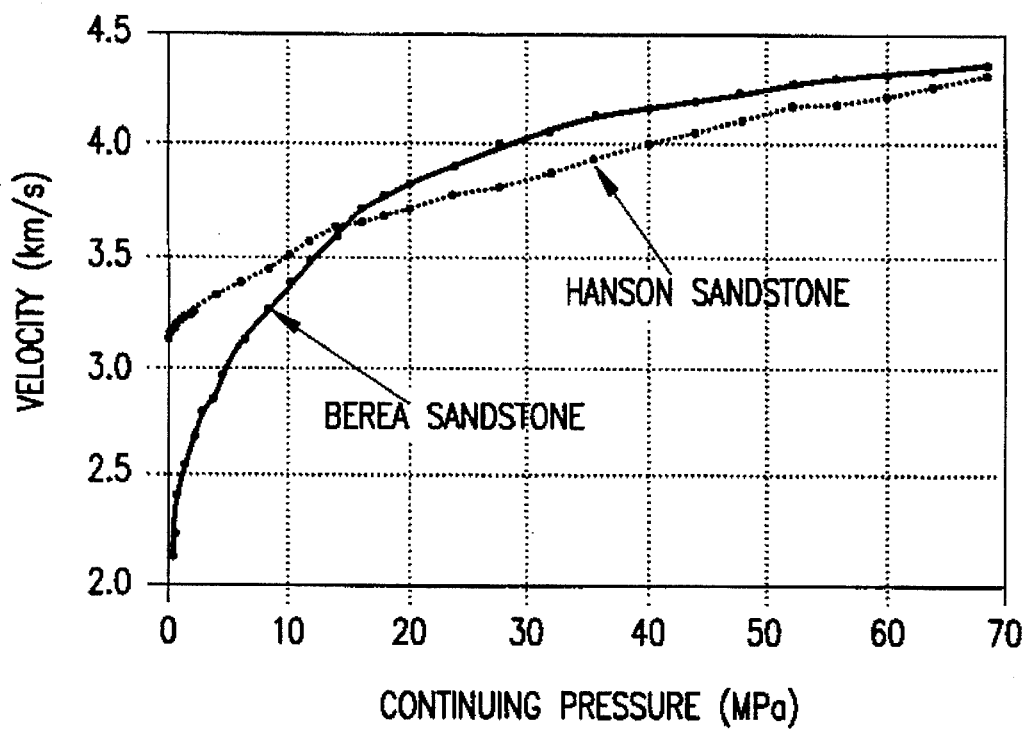
FIG. 4 is a plot of velocity versus hydrostatic stress in Berea and Hanson sandstone formations.

Confirmation that velocity in a formation increases with increasing stress or confining pressure is seen in FIG. 4 where compressional wave velocity is plotted versus confining pressure for a Berea sandstone and for a Hanson sandstone. As seen in FIG. 4, as the hydrostatic stress increases, the compressional wave velocity in the sandstones increase, although the velocity in the Berea sandstone is seen to have a larger dependence on pressure than the velocity in the Hanson sandstone.

With the results as set forth above, the direction of minimum uniaxial stress about the borehole clearly may be obtained from a determination of the azimuthal velocity variations. These minima will quantitatively predict the propagation direction of artifically induced hydrofractures, (i.e., the fractures will propagate in the direction of the velocity minima around the borehole which correspond to the direction of maximum uniaxial stress in the formation away from the borehole) which will aid in the development of low permeability hydrocarbon reservoirs. While simple visual inspection of the raw data is apparently sufficient to locate the velocity minima, it is possible (as seen in FIGS. 2a, 2b, 2c, and 2d) to fit a sine wave (sin 2Θ) or another regular continuous curve to the data or normalized data, and find the minima in that manner. In addition, as set forth below, the deviation of the best fit curve from the sine wave may provide additional desirable information.

Besides utilizing the stress minima about the borehole for predicting hydrofracture propagation, it should be appreciated that the magnitude of the velocity variation azimuthally about the borehole can provide valuable information. In particular, the formations having relatively larger velocity variations are either relatively less consolidated, or the stress in the formation is large. In either case, an indication of potential borehole collapse is provided.

Additional information regarding the formation is obtained by comparing the best fit curve for the azimuth versus velocity data to the sine wave curve fit for that data. As seen in FIGS. 2a, 2b, 3a, and 3b, the velocity maxima of the data are significantly wider than the sine wave maxima, while the velocity minima of the data are significantly narrower and deeper than the sine wave minima. In order to provide a best fit curve, new models have been derived which are based on the known stress variation around the borehole (as set forth in equations 1 and 2) as well as an assumed stress-to-velocity transform. According to a first model, it is assumed that the velocity varies as a power law between the minimum velocity and maximum velocity, with the relation between velocity and stress given according to:

$$V(\sigma) = V_{min} + (V_{max} - V_{min})(\sigma/\sigma_{max})^{1/n}$$

At the borehole wall, r=b. It is also known that $V=V_{max}$ when stress is maximum, and $V=V_{min}$ when stress is minimum. Combining this information yields:

$$V(\Theta) = V_{min} + (V_{max} - V_{min})[(1 - \cos(2\Theta + \Phi)/2]^{1/n}$$

where $\Phi$ is an adjustable parameter which gives the azimuth of the maximum stress direction in the formation (i.e., minimum stress about the borehole), and n is an adjustable parameter which is a measure of the curvature of the velocity versus the stress curve. Typical values of n are in the range of two to three, while n=1 provides a simple sine wave. $V_{min}$ and $V_{max}$ are preferably taken as the minimum and maximum of the measured data, although they could also be adjustable parameters. Performing a least squares fit of this model to the obtained data gives the best fit curve shown in FIGS. 2a, 2b, 3a, and 3b.

A second model assumes that the velocity in the formation about the borehole varies as an exponential between the minimum velocity and maximum velocity, with the relation between velocity and stress given according to:

$$V(\sigma) = V_{min} + (V_{max} - V_{min})[(1 - e^{n(\sigma - \sigma_{min})/S})/(1 - e^{n(\sigma_{max} - \sigma_{min})/S})]$$

where S is uniaxial or tectonic stress of the formation. With the knowledge that at the borehole wall, r=b, and $V=V_{max}$ when stress is maximum, and $V=V_{min}$ when stress is minimum, the exponential model yields:

$$V(\Theta) = V_{min} = (V_{max} - V_{min})[(1 - e^{2n(1 - \cos(2\Theta + \Phi))})/(1 - e^{4n})]$$

where, as before, $\Phi$ is an adjustable parameter which gives the azimuth of the maximum stress direction in the formation (i.e., minimum velocity at the borehole), and n is an adjustable parameter which is a measure of the curvature of the velocity versus the stress curve. As will be appreciated, a least squares fit of this model to the obtained data could be used to find the parameters n and $\Phi$.

Figure 5:
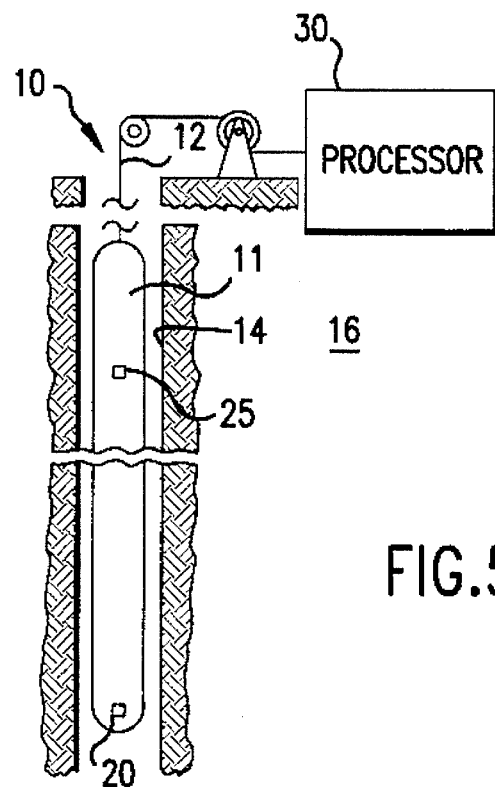
FIG. 5 is a schematic diagram of the sonic borehole tool of the invention for measuring azimuthal stress.

Turning to FIG. 5, a sonic logging tool 10 for conducting a determination of azimuthal velocity and stress about borehole 14 in a formation 16 is seen. The sonic logging tool 10 is shown as including a sonde 11 which is suspended from a conventional wireline cable 12. The sonde has at least one acoustic transducer or transmitter 20, and at least one acoustic receiver or detecting pressure transducer 25. In accord with the invention, the transducer is preferably capable of generating a compressive wave (although shear waves and other waves such as high frequency flexural waves may also be generated), and the receiver is preferably capable of detecting the compressive wave (although shear waves, flexural waves, and other waves may also be detected). Typically in the sonic arts, and in accord with the present invention, the pressure signal detected by the receiver is recorded and processed. The processing may occur downhole by use of a processor (not shown) and/or uphole in processing equipment 30; the information being transmitted uphole via the wireline cable 12. Typically, if processed downhole, a microprocessor is used. When processing uphole, a higher powered processor such as a VAX produced by Digital Equipment Corporation of Brainard, Mass. is used. It is noted that uphole equipment is also used for tracking the depth of the sonde in the borehole. For purposes herein, it should be appreciated that borehole "depth" means the distance from the borehole opening to the surface.

Figure 6A:
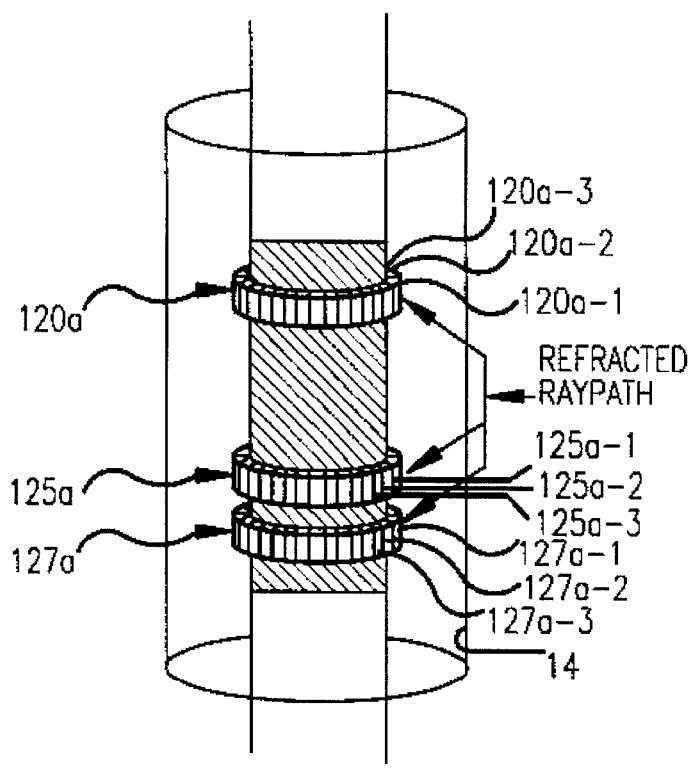
FIG. 6a is a simplified schematic diagram of a first embodiment of the sonde of the sonic borehole tool of the invention.
Figure 6B:
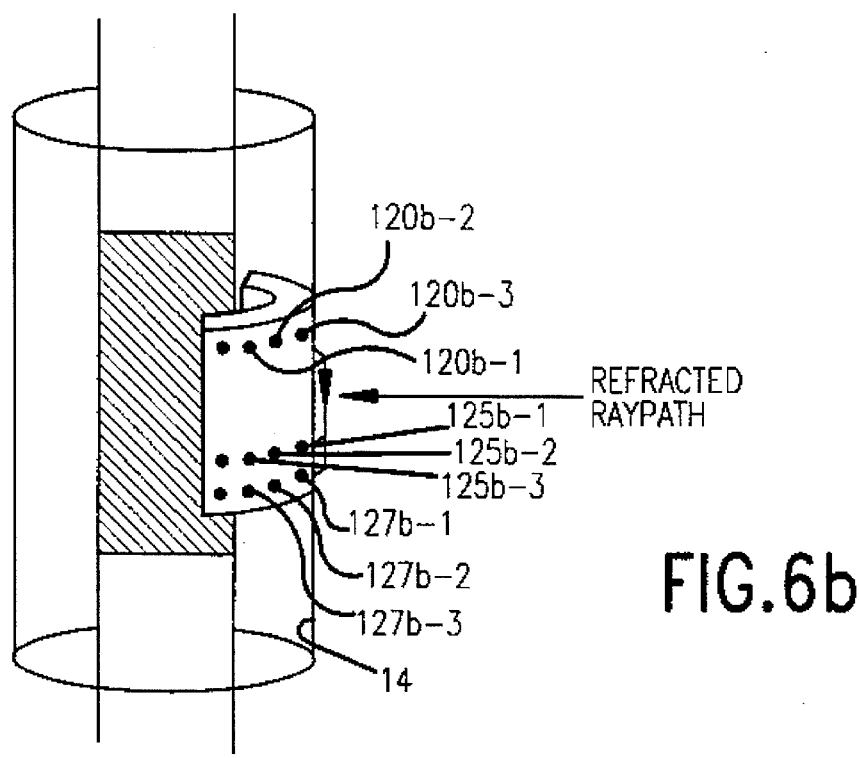
FIG. 6b is a simplified schematic diagram of a second embodiment of the sonde of the sonic borehole tool of the invention.
Figure 6C:
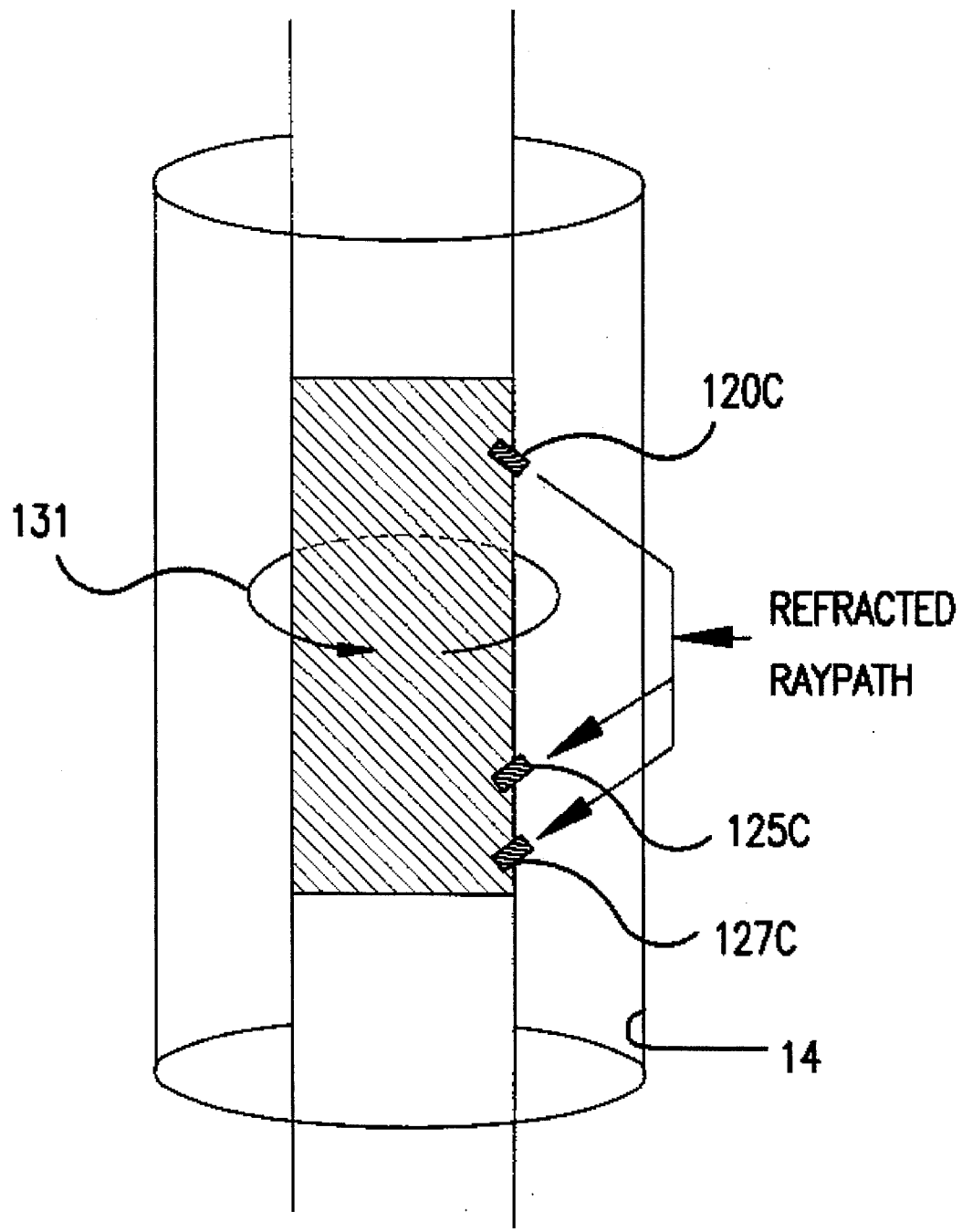
FIG. 6c is a simplified schematic diagram of a third embodiment of the sonde of the sonic borehole tool of the invention.

Three different embodiments of sonde 11 are shown in FIGS. 6a–6c for providing the azimuthal velocity indications required according to the invention. As seen in FIG. 6a, a first embodiment includes a segmented cylindrical transmitter 120a and two axially spaced segmented cylindrical receivers 125a, 127a. Via electronic control (not shown) in the sonde, the segments 120a-1, 120a-2, 120a-3 . . . of the cylindrical transmitter 120a are preferably fired sequentially (although multiple non-adjacent segments may be fired at the same time), and the arriving waveforms are recorded at the corresponding segments 125a-1, 127a-1, 125a-2, 127a-2, 125a-3, 127a-3 of the receivers. By finding the compressional wavefront arrivals at the receivers, and from a knowledge of the distance ($\Delta z$) between the receivers, the velocity of the compressional wave in the formation is determined according to well known techniques. Because the segments are located at different azimuths around the borehole, the velocities for the formation at those azimuths are determined and may either be plotted (uphole) such as seen in FIGS. 2a or 3a, or compared to determine maxima and/or minima. The azimuth of the maximum or minimum velocity may then be presented, if desired, in a log format as a function of borehole depth or distance. It will be appreciated that with the embodiment of FIG. 6a, instead of using segmented cylindrical receivers 125a, 127a, ring receivers may be utilized as only one segment of the segmented cylindrical transmitter 120a is fired at a time. It will also be appreciated that only one receiver 125a is required rather than receivers 125a and 127a, although velocity determinations will not be quite as accurate. Likewise, more than two receivers may be utilized to provide additional accuracy in the formation velocity determinations.

A second embodiment of sonde is seen in FIG. 6b and comprises a pad tool having a plurality of pads 128 (only one shown), each having a plurality of transmitters 120b-1, 120b-2, 120b-3, . . . , and a plurality of receivers 125b-1, 127b-1, 125b-2, 127b-2, 125b-3, 127b-3, . . . The pad design is analogous to the FBI formation imager (see Ekstrom, M. P. et al., "Formation Imaging with Microelectrical Scanning Arrays", Trans. SPWLA, 27th Annual Logging Symposium, June 1986) which permits the pads to be pressed against the borehole wall. As shown in FIG. 6b, two axially spaced receivers (e.g., 125b-2, 127b-2) are preferably provided for each transmitter. With a plurality of pads formation velocity information can be obtained at numerous azimuths around the borehole. In addition, with a plurality of pads, it is possible to simultaneously fire at least one transmitter on each pad, and to make simultaneous velocity measurements at the azimuthally corresponding receivers.

A third embodiment of the sonde is seen in FIG. 6c and utilizes a sonde similar to that of the LWD-Sonic tool disclosed in co-owned U.S. patent application Ser. No. 07/839,969, filed Feb. 20, 1992. The third embodiment includes a single transmitter 120c and two receivers 125c and 127c which are all mounted on the side of the tool and aimed at the borehole wall. As shown in schematic fashion by arrow 131, at least a portion of the tool which contains the transmitter 120c and receivers 125c, 127c is rotatable relative to the borehole so that acoustic velocity measurements may be made at a plurality of azimuths around the borehole.

Figure 7A:
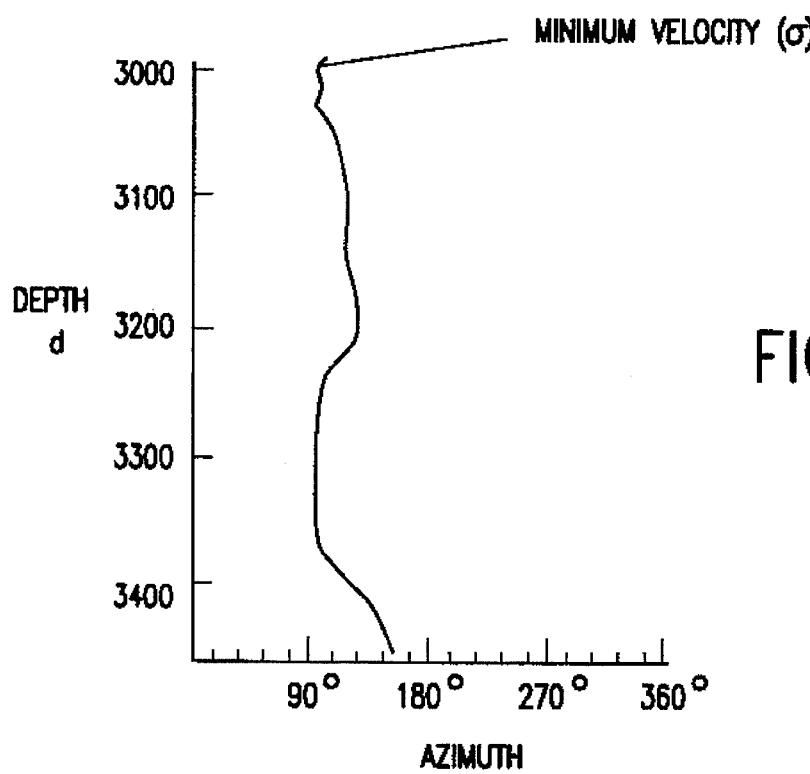
FIG. 7a is a log of azimuths having minimum velocities along a borehole.
Figure 7B:
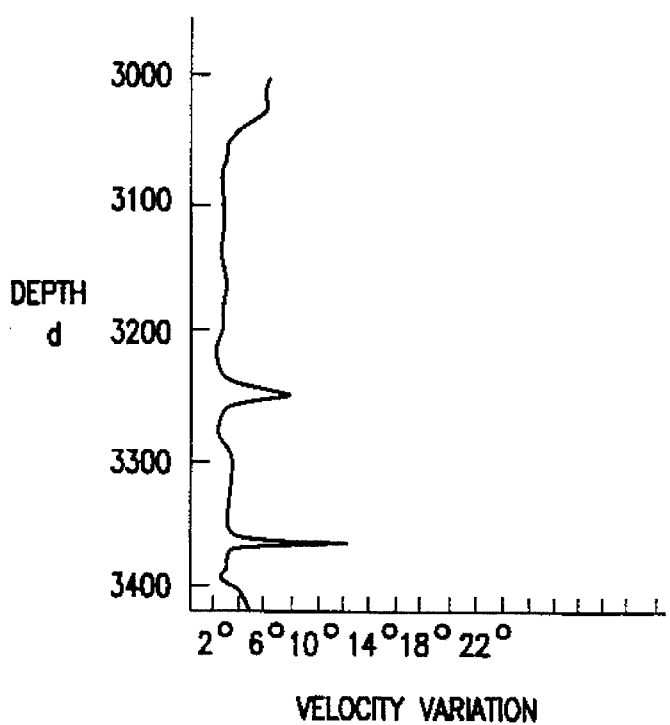
FIG. 7b is a log representing percentage formation velocity variation at particular borehole depths.

Regardless of whether the borehole tool utilizes a single transmitter which is rotated as in FIG. 6c, a segmented transmitter such as in FIG. 6a, or multiple transmitters on a pad such as in FIG. 6b, the pressure information obtained at the receivers is typically forwarded uphole via wireline cable 12 to the processing equipment 30 where azimuthal velocity determinations are made. The azimuthal velocity determinations may then be used in many of different manners. A first use of the velocity determinations is to provide a velocity versus azimuth log (such as in FIGS. 2b and 3b) for the formation at one or more particular depths of interest. As discussed above, much information may then be derived from the provided log. A second use of the velocity determinations is to find the azimuth of the minimum velocity (i.e., minimum stress at the borehole) for the formation at depths of interest, although the maximum velocities (i.e., maximum stress at the borehole) may also be found. The azimuths of maximum or minimum velocity or stress can then be provided in log format over depth such as shown in FIG. 7a. From the log of minimum velocity azimuths, the likely direction of hydrofracture propagation may be determined at different depths in the formation. A third use of the velocity determinations is to determine, for a particular borehole depth, what the formation velocity variation is for that depth. In particular, by having the velocity determinations at the azimuths around the borehole, the difference between the minimum and maximum can be used, and/or the difference can be divided by the minimum or maximum to provide a velocity variation percentage as shown in FIG. 7b. The actual difference and/or the variation percentage can be used to help predict locations of possible borehole collapse. A fourth use of the velocity determinations is to fit a sine wave curve to the velocity versus azimuth data at particular locations and to look at the deviation of the sine wave curve from the actual data. The deviation, which can be quantified if desired, can be used among other things, to also help predict locations of possible borehole collapse. Similarly, a best fit curve utilizing either the power law model or exponential model can be fit to the velocity and azimuth data and utilized to find additional parameters of the formation. For example, if a curve defined by equation (4) is utilized, the adjustable parameter n can be obtained.

As will be appreciated by those skilled in the art, the methods of the invention closely relate to the apparatus inventions set forth above. Generally, the method of the invention comprises utilizing an acoustic borehole tool to find the velocities of the formation as a function of azimuth around the borehole. Using the velocity versus azimuth information, various determinations can be made at any given depth in the borehole, including: azimuthal direction of maximum and/or minimum velocity (stress); actual and/or percentage formation velocity variation; susceptibility to formation failure; and formation parameters.

There have been described and illustrated herein apparatus and methods for measuring the acoustic velocity of a formation as a function of azimuth, and for obtaining useful information therefrom. While particular embodiments of the invention have been described, it is not intended that the invention be limited thereto, as it is intended that the invention be as broad in scope as the art will allow and that the specification be read likewise. Thus, while particular acoustic borehole tools have been disclosed for obtaining velocity information as a function of azimuth about the borehole, it will be appreciated that other tools could be utilized. Also, while an increased acoustic velocity has been used as an indicator of increased stress at the borehole, it will be appreciated that other attributes of an acoustic signal such as amplitude could be utilized to generate a stress indication, which in turn is used for obtaining information regarding the formation. Further, while the compressional velocity is preferred for determining acoustic velocity, it will be appreciated that the shear velocity or high frequency flexural wave velocity could be utilized in lieu thereof. It will also be appreciated that while particular determinations such as direction of hydrofracture propagation, locations of possible borehole collapse, etc., were described as obtainable from the acoustic-velocity/azimuth determinations, yet other determinations can be obtained from the information and/or from the parameters determined. It will therefore be appreciated by those skilled in the art that yet other modifications could be made to the provided invention without deviating from its spirit and scope as so claimed.

I claim:

1. Apparatus for investigating earth formations traversed by a borehole, comprising:
   a) a transmitter for generating acoustic waves at a plurality azimuths about the borehole and for transmitting the acoustic waves into the earth formations;
   b) a receiver axially spaced from the transmitter for receiving, at the plurality of azimuths, the acoustic waves transmitted into the formations near the borehole at the plurality of azimuths; and
   c) a processor coupled to the receiver for determining acoustic velocities of the formations around the borehole as a function of azimuth and finding the azimuth of one of a maximum acoustic velocity and a minimum acoustic velocity and generating at least one indication relating to the earth formations as a result thereof.

2. Apparatus as claimed in claim 1, wherein the transmitter comprises a segmented cylindrical transmitter which generates compressional waves.

3. Apparatus as claimed in claim 2, wherein the receiver comprises a segmented cylindrical receiver.

4. Apparatus as claimed in claim 1, wherein the receiver comprises at least two axially spaced receivers.

5. Apparatus as claimed in claim 4, wherein each of the at least two axially spaced receivers are segmented cylindrical receivers.

6. Apparatus as claimed in claim 1, wherein the apparatus further comprises a sonde having extensible arms and pads pending from the extensible arms, the pads being azimuthally spaced around the borehole, the transmitter comprising a plurality of azimuthally spaced transmitters, the receiver comprising a plurality of azimuthally spaced receivers, and each pad including at least one of the plurality of transmitters and one of the plurality of receivers.

7. Apparatus as claimed in claim 6, wherein each pad includes at least two receivers which are axially spaced from each other at a substantially identical azimuth.

8. Apparatus as claimed in claim 6, wherein each pad includes a plurality of azimuthally spaced transmitters and a plurality of azimuthally spaced receivers, the receivers and transmitters being located at corresponding azimuths.

9. Apparatus as claimed in claim 1, wherein the transmitter and the receiver are (i) directed at the formation, (ii) located at a substantially identical azimuth, and (iii) rotatable in the borehole to a plurality of azimuths about the borehole.

10. Apparatus as claimed in claim 1, wherein the processor further includes means for generating a log of velocity versus azimuth around the borehole at a depth in the borehole.

11. Apparatus as claimed in claim 1, wherein the processor further includes means for generating a log of the azimuth of one of a maximum velocity and a minimum velocity at a plurality of depths in the borehole, the log constituting the at least one indication.

12. Apparatus as claimed in claim 1, wherein the processor further includes means for finding both maximum velocity and minimum velocity at a depth in the borehole and for finding a difference between the maximum velocity and minimum velocity at that depth in the borehole.

13. Apparatus as claimed in claim 12, wherein the processor further includes means for generating a log of differences between maximum and minimum velocities over a plurality of depths in the borehole.

14. Apparatus as claimed in claim 1, wherein the processor further includes means for finding maximum velocity and minimum velocity at a depth in the borehole, determining any difference therebetween, and dividing the difference by one of the maximum velocity and the minimum velocity at that depth in the borehole to provide a percentage velocity variation at that depth in the borehole.

15. Apparatus as claimed in claim 1, wherein the processor further includes means for fitting a sine wave to the acoustic velocities which are a function of azimuth.

16. Apparatus as claimed in claim 15, wherein the processor further includes means for indicating closeness of fit of the sine wave to the acoustic velocities.

17. Apparatus as claimed in claim 1, wherein the processor further includes means for fitting a curve to the acoustic velocities which are a function of azimuth.

18. Apparatus as claimed in claim 17, wherein the curve is defined according to $$V(\Theta)=V_{min}+(V_{max}-V_{min})[(1-\cos(2\Theta+\Phi))/2]^{1/n}$$

where $\Phi$ is the azimuth of the minimum of the acoustic velocities about the borehole, and n is a parameter of the formation, $V_{min}$ is a minimum velocity of the acoustic velocities, and $V_{max}$ is a maximum velocity of the acoustic velocities.

19. Apparatus as claimed in claim 17, wherein the curve is defined according to $$V(\Theta)=V_{min}+(V_{max}-V_{min})[(1-e^{2n(1-\cos(2\Theta+\Phi))})/(1-e^{4n})]$$

where $\Phi$ is the azimuth of the maximum of the acoustic velocities, and n is a parameter of the formation, $V_{min}$ is a minimum velocity of the acoustic velocities, and $V_{max}$ is a maximum velocity of the acoustic velocities.

20. A method for investigating earth formations traversed by a borehole utilizing a borehole tool having a transmitter, a receiver axially spaced from the transmitter, and a processor coupled to the receiver, the method comprising:
   a) generating acoustic waves with the transmitter at a plurality azimuths about the borehole and transmitting the acoustic waves into the earth formations about the borehole;
   b) detecting the acoustic waves at the plurality of azimuths with the receiver;
   c) determining acoustic velocities of the formation around the borehole as a function of azimuth with the processor, finding the azimuth of one of a maximum acoustic velocity and a minimum acoustic velocity, and generating at least one indication relating to the earth formations based thereon.

21. A method as claimed in claim 20, wherein the indication is recorded at a plurality of depths in the borehole.

22. A method as claimed in claim 20, further comprising obtaining a velocity variation by comparing a maximum velocity with a minimum velocity.

23. A method as claimed in claim 22, further comprising generating a log of the velocity variation over a plurality of depths in the borehole.

24. A method as claimed in claim 20, further comprising determining any difference between maximum and minimum velocities and dividing the difference by one of the maximum velocity and the minimum velocity to provide a percentage velocity variation.

25. A method as claimed in claim 20, further comprising fitting a sine wave to the acoustic velocities which are a function of azimuth.

26. A method as claimed in claim 25, further comprising determining closeness of fit of the sine wave to the acoustic velocities.

27. A method as claimed in claim 20, further comprising fitting a curve to the acoustic velocities which are a function of azimuth, the curve being defined according to $$V(\Theta) = V_{min} + (V_{max} - V_{min})[(1 - \cos(2\Theta + \Phi))/2]^{1/n}$$

where $\Phi$ is the azimuth of the minimum of the acoustic velocities about the borehole, and n is a parameter of the formation, $V_{min}$ is a minimum velocity of the acoustic velocities, and $V_{max}$ is a maximum velocity of the acoustic velocities.

28. A method as claimed in claim 20, further comprising fitting a curve to the acoustic velocities which are a function of azimuth, the curve being defined according to $$V(\Theta) = V_{min} + (V_{max} - V_{min})[(1 - e^{2n(1-\cos(2\Theta + \Phi))})/(1 - e^{4n})]$$

where $\Phi$ is the azimuth of the minimum of the acoustic velocities about the borehole, and n is a parameter of the formation, $V_{min}$ is a minimum velocity of the acoustic velocities, and $V_{max}$ is a maximum velocity of the acoustic velocities.

\* \* \* \* \*